United States Patent [19]

Goudriaan et al.

[11] Patent Number: 4,683,121
[45] Date of Patent: Jul. 28, 1987

[54] REACTOR FOR NON-ISOTHERMIC REACTIONS FOR THE PREPARATION OF HYDROCARBONS

[75] Inventors: Johan C. Goudriaan; Maarten J. Van der Burgt, both of The Hague, Netherlands

[73] Assignee: Shell Oil Company, Houston, Tex.

[21] Appl. No.: 736,908

[22] Filed: May 22, 1985

[30] Foreign Application Priority Data

May 29, 1984 [GB] United Kingdom ............... 8413596

[51] Int. Cl.$^4$ ............................................. B01J 8/06
[52] U.S. Cl. ................................. 422/197; 422/196; 422/311
[58] Field of Search .................. 422/196, 197, 311; 239/391, 498, 518, 520

[56] References Cited

U.S. PATENT DOCUMENTS

| | | | |
|---|---|---|---|
| 3,532,472 | 10/1970 | Foster | 422/197 |
| 3,825,188 | 7/1974 | Doering | 239/498 |
| 3,831,861 | 8/1974 | Hanson, Jr. | 239/520 |
| 4,252,276 | 2/1981 | Aprea | 239/391 |
| 4,256,783 | 3/1981 | Talcada et al. | 422/197 |
| 4,505,879 | 3/1985 | Lhonoré et al. | 422/241 |

FOREIGN PATENT DOCUMENTS 2048108 12/1980 United Kingdom .

*Primary Examiner*—Barry S. Richman
*Assistant Examiner*—William R. Johnson
*Attorney, Agent, or Firm*—Kimbley L. Muller

[57] ABSTRACT

A reactor having a vertically extending vessel wall (2) is provided with a plurality of staggered elongated parallel tubes (8) adapted for being filled with catalyst material and substantially vertically extending between an upper tube plate (10) and a lower tube plate (9), means (12, 13) for circulating a heat transfer medium between the tube plates (9, 10) alongside the tube walls (8), inlet means (3, 17, 18) above the parallel tubes (8) for distributing fluid in the form of one or more sprays and gas over the plurality of tubes (8) and outlet means (4, 20) situated below the plurality of tubes (8) for removal of fluids from the reactor, wherein the plurality of staggered tubes (8) are arranged in rows such that the tubes of adjacent rows are staggered, and wherein upper tube plate (10) is provided with openings (15), having a lower part in which the tubes (8) are closely fitted and having a substantially concentric upper part diverging in upward direction, the upper ends of the adjacent openings having edges in common in such a manner that the upper end of the upper tube plate (10) is formed by edges (16) arranged in a hexagonal honeycomb ribbed configuration.

9 Claims, 3 Drawing Figures

REACTOR FOR NON-ISOTHERMIC REACTIONS FOR THE PREPARATION OF HYDROCARBONS

FIELD OF INVENTION

The present invention relates to a reactor suitable for carrying out exothermic or endothermic reactions in the mixed gas/liquid phase, the reactor being of the type provided with a bundle of vertical tubes extending between tube plates for reaction media, the tubes being normally filled with catalyst material. Generally reaction medium is caused to flow in downward direction through the tubes of such a reactor and reaction product is removed from the bottom-part of the reactor.

There is seemingly an increasing demand for larger capacity equipment, not only because all chemical processes are carried out on ever larger scale, but also because certain processes are increasingly used, such as the synthesis of hydrocarbons for which the present reactor was initially designed. The market price of crude oil has in the recent past reached a level so high that alternative processes for the preparation of hydrocarbons, such as from the conversion of carbon monoxide and hydrogen prepared by gasification of coal, attract increasing interest.

Upscaling of a reactor of the above type to increase the capacity thereof may, however, have a severe adverse influence on the efficiency, particularly if the reactor is used for carrying out highly endothermic or exothermic reactions. In highly exothermic reactions, the heat liberated should preferably be removed continuously to avoid undesirably high temperatures which might cause a sharp reduction in the rate of reaction and/or the occurrence of unwanted side reactions. The aim of continuous heat removal, in exothermic reactions, or heat supply, in endothermic reactions, means with respect to tube type reactors, that the tubes forming the reaction zones must have a relatively small cross-sectional area with a heat transfer medium circulated around the outer surfaces of the tubes. If the cross-sectional areas of the reaction zones are large, the middle parts of the zones are too far away from the heat transfer medium at the outside of said zones and hence tend to experience undesirable temperature increases or temperature drops. Increase in the capacity of a tube type reactor should therefore be accomplished by an increase of the number of tubes rather than by an increase of the tube diameters.

The use of a large number of tubes enclosed in a necessarily large diameter reactor vessel presents however, a number of problems. First, it becomes difficult to achieve uniform distribution of heat transfer medium over the full diameter of the reactor vessel. Second, uniform distribution of liquid over the various tubes becomes more difficult. A uniform distribution of heat transfer medium along the tubes is required to obtain a reaction product with a predetermined constituency and to prevent stresses in the bundles of tubes due to temperature differences.

If a tube type reactor is intended to be used with a liquid, optionally a liquid reaction medium, in addition to a gaseous reaction medium, care should be taken that the liquid is not only uniformly distributed over the tubes of the reactor but is also uniformly distributed over the cross-section of each of the tubes. The liquid intended to be passed through the tube bundles of a tube type reactor is normally supplied via the nozzles of a liquid distribution system in the form of a mist to the tubes. In large diameter reactors, the formed mist of liquid may easily be maldistributed over the tubes due to even very slight inclination of the reactor vessel itself or of the upper tube sheet supporting the bundle of tubes.

OBJECTS OF THE INVENTION

An object of the present invention is to overcome problems encountered with increasing the capacity of tube type reactors suitable for operation with a liquid passing through the tubes and suitable for carrying out exothermic or endothermic reactions.

An embodiment of this invention resides in an apparatus for performing a chemical reaction in a reaction vessel, which reaction vessel comprises a normally vertically extending outer vessel wall, a fluid collection zone situated in the bottom of said vessel, a perforated upper tube plate situated in the upper portion of said vessel, a lower tube plate permeable by fluids but impermeable to solid material situated in the lower portion of said vessel, means for circulating a heat transfer medium situated intermediate said upper and lower tube plates, a fluid introduction zone having fluid inlet means comprising a plurality of spray nozzles and a fluid inlet means situated in said vessel at a point elevated with respect to said upper tube plate, a fluid outlet means situated in the bottom of said vessel, and a plurality of staggered parallel tubes extending from and in intercommunication with said upper tube plate and extending to a point in contact with said lower tube plate, wherein said staggered tubes are in intercommunication with said upper plate through a plurality of respective openings in said upper plate, said openings having an upper part and a lower part, wherein said lower part is closely fitted to the top portion of said respective parallel tube and wherein said upper part is substantially concentric with said lower part and diverging in an upward direction to an upper end, said upper end being situated contiguous to and adjacent with respect to the edges of other upper ends of said openings to form a hexagonal honeycomb configuration in said upper tube plate.

Another embodiment of this invention resides in an apparatus for performing a chemical reaction between reactants in an elongated upright vessel having a vertical axis, a fluid inlet in the top of said vessel and a fluid outlet in the bottom of said vessel, which comprises: a perforate upper tube plate situated in the upper portion of said vessel transverse to said vertical axis of said vessel having honeycomb hexagonal-shaped ribbed openings hereafter more specifically defined; a perforate lower tube plate situated in the lower portion of said vessel transverse to said vertical axis of said vessel having openings permeably selective for fluids and impermeable to solid particle material; a means for introducing, circulating and withdrawing a heat transfer medium intermediate said perforate upper tube plate and said lower tube plate with respective baffles situated intermediate said upper and said lower tube plate to provide that said heat transfer medium passes axially alongside a set of hereinafter defined parallel catalyst tubes and to prevent said heat transfer medium from penetration of either said upper tube plate or lower tube plate; a fluid collection zone situated at a lower elevation with respect to said lower tube plate and in communication with said fluid outlet; a fluid introduction zone situated at a higher elevation with respect to said upper tube plate having a fluid introductory conduct containing a plurality of fluid spray nozzles and a plurality of staggered elongated parallel tubes receptive for solid particulate catalyst material in communication with said upper tube plate and said lower tube plate, wherein said catalyst is impermeable to passage through said lower tube plate and wherein said elongated parallel tubes are in attachment with said upper tube plate by a plurality of openings situated in said upper tube plate, said openings defined by an upper part of said opening substantially concentric with a lower part of said opening with said upper part diverging in an upward direction to an upper end of said opening to form a plurality of hexagonal honeycomb openings having edges contiguous to and adjacent to one another to form a honeycomb hexagonal-shaped ribbed configuration in said upper tube plate to insure that fluid egressing from said surmounted spray nozzles of said fluid introduction zone flow directly downward into said respective parallel tube with deminimis sideflow of said fluid.

BRIEF DESCRIPTION OF THE INVENTION

This invention relates to a chemical reactor having a downflow direction of reactant passage with frustoconical perforations in an upper plate such that the upper and lower parts of the openings or holes are substantially coaxially arranged with respect to one another. A honeycomb configuration is provided by continuous alignment of the tops of the openings.

DETAILED DESCRIPTION OF THE INVENTION

The reactor of this invention comprises a normally vertically extending vessel provided with a plurality of parallel tubes adapted for being filled with catalyst material and substantially vertically extending between an upper tube plate and a lower tube plate, means for circulating a heat transfer medium between the tube plates along the tubes, inlet means above the tubes for distributing liquid in the form of one or more sprays and gas over the plurality of tubes and an outlet below the plurality of tubes for removal of liquid and gas from the vessel, wherein the plurality of tubes are arranged in rows such that the tubes of adjacent rows are staggered, and wherein the upper tube plate is provided with openings having a lower part in which the tubes are closely fitted and having a substantially concentric upper part diverging in an upward direction, the upper ends of adjacent openings having edges in common in such a manner that the upper end of the upper tube plate is formed by edges of the openings arranged in a hexagonal configuration.

The invention further relates to a process for the preparation of hydrocarbons from a mixture of hydrogen and carbon monoxide with the aid of a catalyst, wherein the catalyst is arranged in the tubes of a reactor according to the invention and liquid is introduced into the reactor via a liquid inlet means above the tubes.

The reactor according to the invention is most effectively filled with reaction tubes since these tubes are arranged in a staggered position. Apart from a high capacity, the proposed arrangement of the tubes has a further advantage in that the tubes can be most efficiently cooled or heated by the heat transfer medium passing alongside the tubes. With the proposed arrangement of the reaction tubes, the complete peripheries of the tubes are intensively contacted with heat transfer medium. In this respect it should be noted that in a non-staggered configuration of the reaction tubes the heat transfer medium will preferentially flow between the rows of tubes, so that the opposite surfaces of the tubes of a row are less contacted with heat transfer medium.

A further important aspect of the proposed reactor resides in the configuration of the upper tube plate. According to this invention, the upper parts of the holes or openings in the upper tube plate are frustoconically shaped or cup shaped. Each of the openings in which the tubes are positioned has edges so that the edges of adjacent openings contact each other and the upper tube plate has a honeycomb shape with hexagonal ribs. This configuration of the upper tube plate is essential for an optimal distribution of liquid sprayed onto the upper tube plate. Liquid cannot flow over the tube plate in sideward direction but will flow directly downward via the widened openings in the tube plate into the tubes. In this connection it should be understood that the arrangement of a perfectly horizontal tube plate in large diameter reactors is hardly feasible from the point of view of construction. A slight inclination of the tube plate is difficult to avoid. With the proposed honeycomb configuration of the openings in the tube plate, however, such an inclination will not adversely influence the uniformity of liquid distribution over the tubes provided that the reactant liquid is uniformly sprayed above the tube plate. By this structure, all tubes will receive equal quantities of liquid irrespective of a slight inbalance of the horizontal position of the upper tube plate.

The tubes may be secured in the lower parts of the openings in any suitable manner, such as for example, by welding. The height of the openings and thus the thickness of the tube plate should be chosen dependent of the reactor width. Increase of the reactor width should be accompanied by an increase of the height of the inside walls of the openings to correct for deflections in the preferred horizontal positions of the upper tube plate.

According to a suitable embodiment of the invention, the reactor is provided with a liquid distributing system arranged above the upper tube plate and comprising a plurality of substantially equally spaced nozzles each having an outlet passage facing the upper tube plate and being bounded by a peripheral downwardly widening surface having the shape of a hexagonal in horizontal cross-section. The height of the nozzles above the upper tube plate and/or the number and mutual distance between the nozzles should preferably be chosen in such a manner that the sprays of adjacent nozzles touch each other at the upper surface of the upper tube plate. The above nozzles producing sprays with a hexagonal pattern in cross-section have a number of advantages over known spray nozzles producing sprays with patterns being circular or square in cross-section. Overlapping sections of sprays from adjacent nozzles, occurring when liquid has to be evenly distributed over a surface using nozzles producing sprays with circular pattern, can be overcome by using the proposed nozzles. Although overlapping sections can also be prevented by using square nozzle outlet openings, the latter have the disadvantage that the generated sprays are less homogeneous than the sprays obtainable with the hexagonal spray pattern producing nozzles.

DETAILED DESCRIPTION OF THE DRAWINGS

Figure 1:
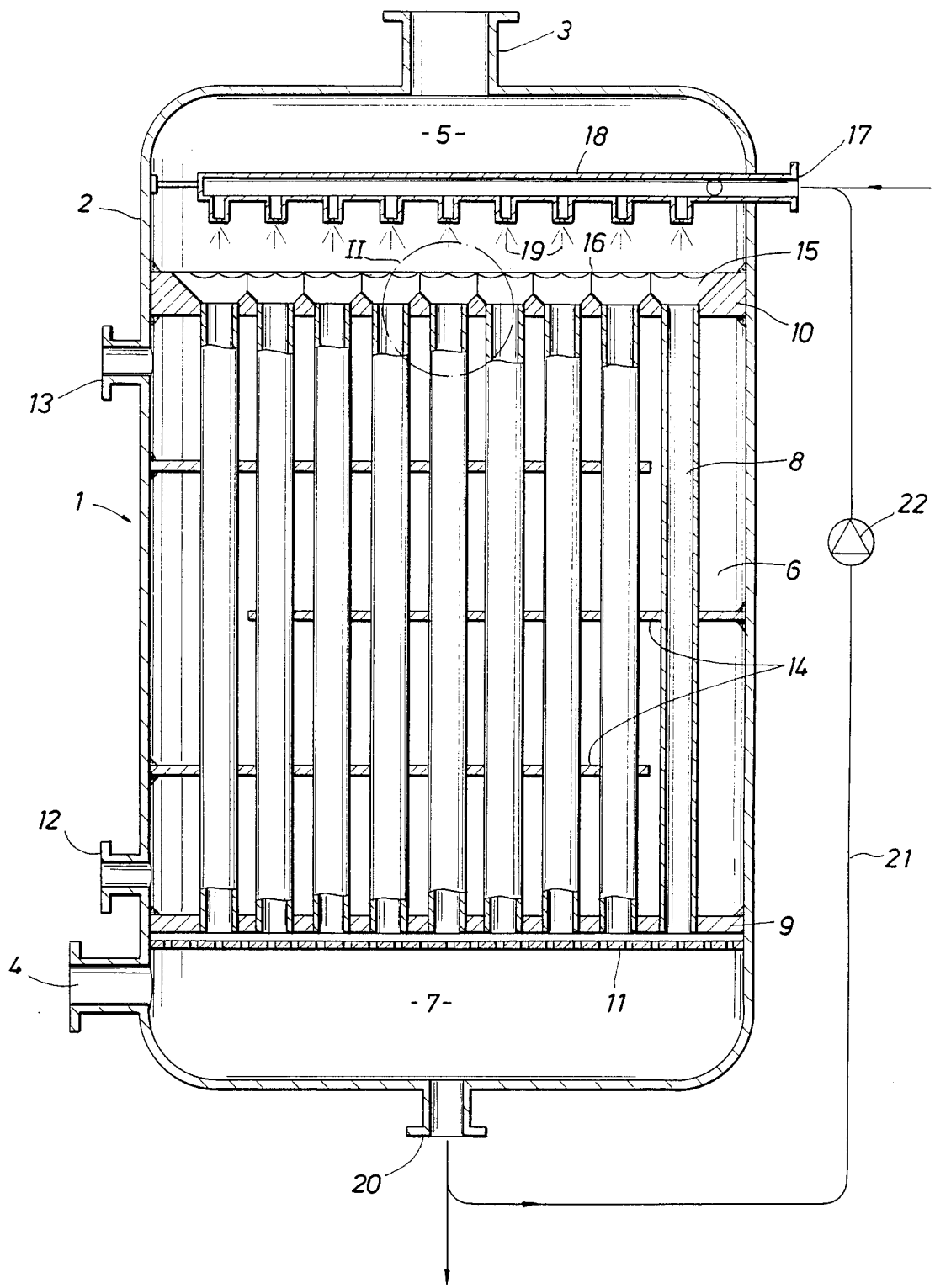
FIG. 1 is a vertical cross-section of an embodiment of a reactor according to the invention.
Figure 2:
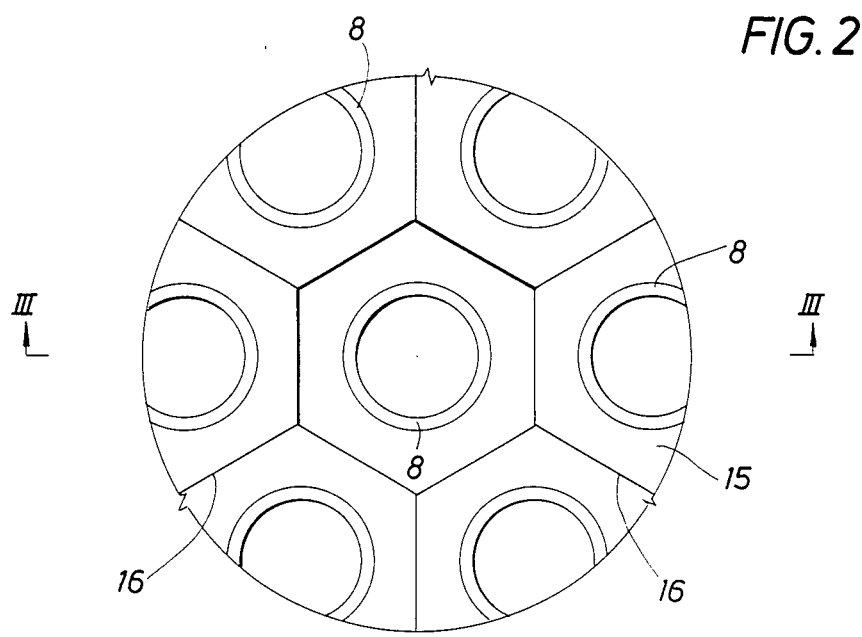
FIG. 2 shows a top view of detail II shown in FIG. 1 on a larger scale than the scale of FIG. 1.
Figure 3:
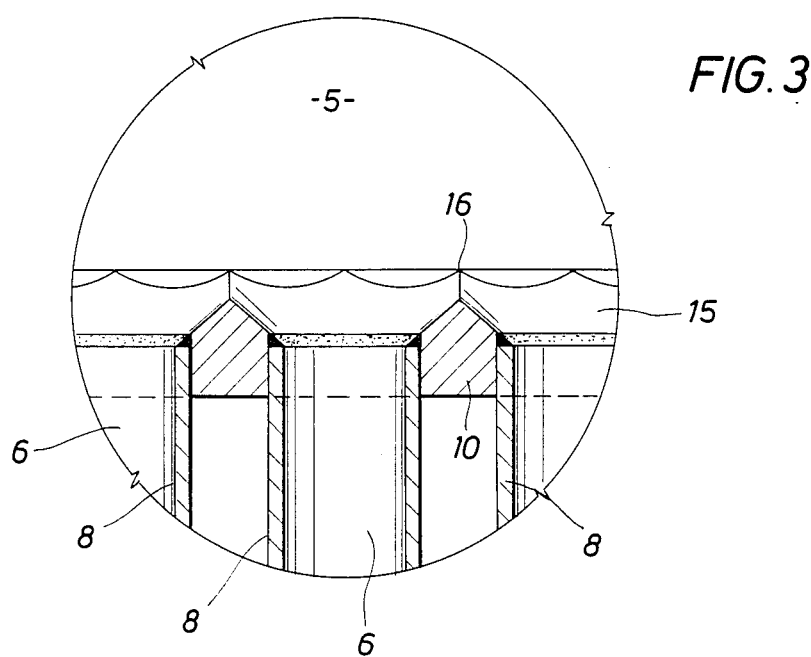
FIG. 3 shows cross section III—III of FIG. 2.

Referring to the Figures, a reactor 1 is shown comprising a cylindrical vessel 2 with an inlet 3 at the upper part of the vessel for fluid reaction media and an outlet 4 in the lower part of the vessel for gaseous and/or liquid fluid reaction product. The interior of the vessel is subdivided into three vertically spaced zones, viz. a fluid introductory zone 5, a reaction zone 6 and a fluid collecting zone 7. The reaction zone 6 is provided with a plurality of parallel vertical reaction tubes 8 arranged between and supported by a lower tube plate 9 and an upper tube plate 10. The tubes of the various rows are positioned in a staggered arrangement as clearly shown in FIG. 3. The reaction tubes may be filled with catalyst material, supported at the lower ends of the tubes 8 by for example a gridlike structure 11 permeable to liquid and gas and impermeable to catalyst material. The vessel 2 is further provided with an inlet 12, an outlet 13 and a plurality of guiding plates 14 for circulating a heat transfer medium along the tubes in the reaction zone 6.

The tubes 8 closely fit in the lower substantially circular parts of openings 15 drilled in the upper tube plate 10. The upper parts of the holes or openings 15 are substantially frusto-conically shaped in such a manner that the upper parts and the lower parts of the openings are substantially coaxically arranged with respect to each other. A description of how to construct openings of gradually increasing surface area is made in British Pat. No. 2,048,108 all of the teachings of which are now incorporated by reference. The frusto-conical parts of the openings 15 have a widening of such magnitude that the edges of said opening parts contact each other so that each opening which is fully surrounded by adjacent openings has its upper end formed by ribs 16 arranged in a hexagonal pattern. Due to this arrangement the upper surface of the upper tube plate 10 is separated in hexagonal form like a honeycomb, whilst the horizontal surface parts are formed by only the upper ends of the ribs 16.

The vessel 2 is further provided with a liquid inlet 17 in the fluid introductory zone 5, which liquid inlet 17 comprises a branched pipe system 18 at its lower end provided with a plurality of outlet nozzles 19, adapted to emit liquid sprays with hexagonal spray pattern in horizontal cross-section. The outlet nozzles 19 are positioned at a mutual distance such that during operation the sprays from the nozzles form a closed and substantially uniform layer of liquid droplets at the entries of the openings 15. Reference is herein made to U.S. Pat. Nos. 3,825,188, 4,252,276 and 3,831,861, all of the teachings of which are herein incorporated by reference, for a description of how to construct spray nozzles or liquid spray heads to obtain a specific type of honeycomb spray configuration.

In the shown embodiment of the invention, the reactor 1 is further provided with a liquid outlet 20 being in fluid communication with a recycle line 21 and pumping means 22 for the recirculation of liquid from fluid collecting zone 7 to fluid introductory zone 5. The recirculation of liquid increases the heat transfer rate over the walls of reaction tubes 8 and cleaning of catalyst particles if the reactor is used for catalytic chemical reactions. Liquid may also form part of the reaction medium, in which case liquid is supplied from a not shown separate liquid source.

The reactor according to the invention is suitable for all kinds of reactions in which heat has to be exchanged. The proposed reactor is in particular suitable for exothermic catalytic reactions, such as the synthesis of methanol, where apart from a gas phase a liquid phase is present during the reaction. More in particular, the reactor is very suitable for the synthesis of hydrocarbons from synthesis gas to form a substitute for petroleum hydrocarbons, wherein liquid is added to the gaseous feedstock for optimizing the process.

What we claim as our invention is:

1. An apparatus for performing a chemical reaction in a reaction vessel, which reaction vessel comprises a normally vertically extending outer vessel wall, means defining a fluid collection zone situated in the bottom of said vessel, an upper tube plate situated in the upper portion of said vessel with means defining a plurality of hexagonal openings having a honeycomb configuration within said upper tube plate, a lower tube plate permeable by fluids but impermeable to solid material situated in the lower portion of said vessel, means for circulating a heat transfer medium situated intermediate said upper and lower tube plates, a fluid introduction zone having fluid inlet means comprising a plurality of inlet fluid spray nozzles situated in axial alignment with said plurality of openings in said upper plate and designed to emit a spray pattern for spray of said inlet fluid in a hexagonal honeycomb configuration substantially congruent to the honeycomb configuration of hexagonal openings to provide for passage directly downward in said hexagonal openings in said upper tube plate and thereby uniform distribution of said inlet fluid over said upper tube plate and to thereby inhibit sideward flow of said inlet fluid over said tube plate and a fluid inlet means situated in said vessel at a point elevated with respect to said upper tube plate, a fluid outlet means situated in the bottom of said vessel, and a plurality each having a top portion of staggered parallel tubes and extending from and in intercommunication with a respective one of said hexagonal openings in said upper tube plate and extending to a point in contact with said lower tube plate, wherein said staggered tubes are in intercommunication with said upper plate through said plurality of hexagonal openings in said upper plate, each of said hexagonal openings having an upper part and a lower part, wherein said lower part is closely fitted to the top portion of a respective parallel tube and wherein said upper part is substantially concentric with said lower part and diverging in an upward direction to an upper end, said upper end being situated contiguous to and adjacent with respect to the edges of other upper ends of said openings to define said honeycomb configuration in said upper tube plate.

2. The apparatus of claim 1 wherein each of said plurality of hexagonal openings in said upper tube plate are shaped in a substantially frusto-conically configuration.

3. The apparatus of claim 1 wherein each of said plurality of hexagonal openings in said upper tube plate are shaped in a substantially honeycomb cup-shaped configuration.

4. The apparatus of claim 1 wherein said plurality of spray nozzles in said fluid introductory zone means are situated in relatively equal spaced relationship with the outlet passage of said nozzles facing downward toward said upper tube plate.

5. An apparatus for performing a chemical reaction between reactants in an elongated upright vessel having a vertical axis, a fluid inlet in the top of said vessel and a fluid outlet in the bottom of said vessel, which comprises:
   a. an upper tube plate situated in the upper portion of said vessel transverse to said vertical axis of said vessel and having means defining a plurality of hexagonal shaped openings having a honeycomb configuration;
   b. a perforate lower tube plate situated in the lower portion of said vessel transverse to said vertical axis of said vessel having means defining openings permeably selective for fluids and impermeable to solid particle material;
   c. a means for introducing, circulating and withdrawing a heat transfer medium intermediate said perforate upper tube plate and said lower tube plate with respective baffles situated intermediate said upper and said lower tube plate to provide that said heat transfer medium passes axially alongside a set of hereinafter defined parallel catalyst tubes and to prevent said heat transfer medium from penetration of either said upper tube plate or lower tube plate;
   d. a fluid collection zone situated at a lower elevation with respect to said lower tube plate and in communication with said fluid outlet;
   e. a plurality of staggered elongated parallel tubes receptive for solid particulate catalyst material in communication with said upper tube plate and said lower tube plate, wherein said catalyst is impermeable to passage through said lower tube plate and wherein said elongated parallel tubes are in attachment with said upper tube plate by said plurality of hexagonal openings situated in said upper tube plate said openings defined by:
   f. an upper part of each of said hexagonal opening substantially concentric with a lower part of said opening with said upper part diverging in an upward direction to an upper end of said opening to form a plurality of hexagonal honeycomb openings having edges contiguous to and adjacent to one another to define said honeycomb configuration in said upper tube plate to insure that fluid egressing from said surmounted spray nozzles of said fluid introduction zone flows directly downward into said respective parallel tube with deminimis sideflow of said fluid; and
   g. a fluid-introduction zone situated at a higher elevation with respect to said upper tube plate having a fluid introductory conduit containing a plurality of fluid spray nozzles situated in axial alignment with said hexagonal openings and designed to emit a spray pattern for spray of said inlet fluid in a hexagonal configuration substantially congruent to said honeycomb configuration within said upper tube plate to provide passage directly downward into said hexagonal openings in said upper plate and thereby uniform distribution of said inlet fluid over said upper tube plate and to thereby inhibit sideward flow of said inlet fluid over said upper tube plated.

6. The apparatus of claim 5 wherein said plurality of staggered elongated parallel tubes are individually separated by imperforate spaces at the top of said tubes at said upper tube plate and at the bottom of said tubes at said lower tube plate.

7. The apparatus of claim 5 wherein said fluid collection zone has a secondary fluid outlet means.

8. The apparatus of claim 7 wherein said secondary outlet means is in direct communication with said fluid introduction zone through a fluid recycle conduit.

9. The apparatus of claim 8 wherein said fluid recycle conduit further includes a pump means to enable recycle of fluid through said recycle conduit from said secondary outlet means to said fluid introduction zone.

* * * * *